(12) United States Patent
Einarsson et al.

(10) Patent No.: US 8,328,745 B2
(45) Date of Patent: Dec. 11, 2012

(54) LEG SUPPORT

(75) Inventors: Palmi Einarsson, San Juan Capistrano, CA (US); Arni Thor Ingimundarson, Ladera Ranch, CA (US)

(73) Assignee: Ossur HF, Reykjavik (IS)

(*) Notice: Subject to any disclaimer, the term of this patent is extended or adjusted under 35 U.S.C. 154(b) by 618 days.

(21) Appl. No.: 12/466,010

(22) Filed: May 14, 2009

(65) Prior Publication Data

US 2009/0287125 A1    Nov. 19, 2009

Related U.S. Application Data

(60) Provisional application No. 61/071,718, filed on May 14, 2008, provisional application No. 61/119,480, filed on Dec. 3, 2008.

(51) Int. Cl.
*A61F 5/00* (2006.01)
*A61F 13/00* (2006.01)
(52) U.S. Cl. .................. 602/23; 602/5; 602/16; 602/26
(58) Field of Classification Search .................. 602/23, 602/5, 60, 65, 20, 26–29; 128/881, 882
See application file for complete search history.

(56) References Cited

U.S. PATENT DOCUMENTS

| | | |
|---|---|---|
| 4,256,097 A | 3/1981 | Willis |
| 4,691,697 A | 9/1987 | Arensdorf et al. |
| RE32,650 E | 4/1988 | Waddell |
| 4,854,308 A | 8/1989 | Drillio |
| 5,007,415 A | 4/1991 | Marion |
| 5,088,479 A | 2/1992 | Detoro |
| 5,486,157 A | 1/1996 | DiBennedetto |
| 5,545,127 A | 8/1996 | DeToro |
| 5,547,464 A | 8/1996 | Luttrell et al. |
| 5,593,383 A | 1/1997 | DeToro |
| 5,653,680 A | 8/1997 | Cruz |
| 5,733,249 A | 3/1998 | Katzin et al. |
| 5,908,398 A | 6/1999 | DeToro |
| 5,944,679 A | 8/1999 | DeToro |
| 6,080,123 A | 6/2000 | Pansiera |
| 6,102,881 A | 8/2000 | Quackenbush et al. |

(Continued)

FOREIGN PATENT DOCUMENTS

CN    2173603 Y    8/1994

(Continued)

OTHER PUBLICATIONS

The Pentagon™ Five Function Knee Orthosis, Product Brochure from Twenty Years 1990-2010 Anatomical Concepts, Inc., p. 30 as of Oct. 10, 2010.

*Primary Examiner* — Kim M Lewis
(74) *Attorney, Agent, or Firm* — Bacon & Thomas, PLLC

(57) ABSTRACT

A leg support adapted to be secured to a leg includes an elongate strut having first and second segments, and a flexible middle segment located therebetween. The strut is arranged for securing to a posterior side of a leg and is centrally located along a medial-lateral plane of a leg. A resilient element is removably secured to a first surface of the strut, and extends across the middle strut segment. The middle strut segment and the resilient device are arranged to correspond to a knee of a leg and bend therewith such that the resilient device urges the strut into a generally upright configuration.

20 Claims, 10 Drawing Sheets

U.S. PATENT DOCUMENTS

| | | | |
|---|---|---|---|
| 6,129,690 A | 10/2000 | Hamlin et al. |
| 6,245,034 B1 | 6/2001 | Bennett et al. |
| 6,302,858 B1 | 10/2001 | DeToro et al. |
| 6,350,246 B1 | 2/2002 | DeToro et al. |
| 6,377,178 B1 | 4/2002 | DeToro et al. |
| 6,409,693 B1 | 6/2002 | Brannigan |
| 6,409,695 B1 | 6/2002 | Connelly |
| 6,464,659 B1 | 10/2002 | DeToro et al. |
| 6,471,664 B1 | 10/2002 | Campbell et al. |
| 6,537,237 B1 | 3/2003 | Hopkins et al. |
| 6,589,195 B1 | 7/2003 | Schwenn et al. |
| 6,635,024 B2 | 10/2003 | Hatton et al. |
| 6,752,774 B2 | 6/2004 | Townsend et al. |
| 6,793,638 B1 | 9/2004 | DeToro et al. |
| 6,824,523 B2 | 11/2004 | Carlson |
| 6,839,906 B2 | 1/2005 | Gold et al. |
| 6,936,020 B2 | 8/2005 | Davis |
| 6,969,363 B2 | 11/2005 | Houser |
| 6,969,365 B2 | 11/2005 | Scorvo |
| 7,033,330 B2 | 4/2006 | de Lint |
| 7,048,704 B2 | 5/2006 | Sieller et al. |
| 7,083,583 B2 | 8/2006 | Opahle et al. |
| 7,112,180 B2 | 9/2006 | Guenther |
| 7,112,181 B1 | 9/2006 | DeToro et al. |
| 7,122,016 B1 | 10/2006 | DeToro et al. |
| 7,150,721 B2 | 12/2006 | Houser |
| 7,207,960 B2 | 4/2007 | Kenney |
| 7,309,322 B2 | 12/2007 | Albrecht et al. |
| 7,662,119 B2 | 2/2010 | DeToro et al. |
| 7,682,322 B2 | 3/2010 | Engelman |
| 2003/0093018 A1 | 5/2003 | Albrecht et al. |
| 2004/0260220 A1 | 12/2004 | Wagner et al. |
| 2005/0033208 A1 | 2/2005 | Jacobs |
| 2006/0046910 A1 | 3/2006 | Rastegar et al. |
| 2006/0142680 A1 | 6/2006 | Iarocci |
| 2006/0206043 A1 | 9/2006 | Yakimovich et al. |
| 2006/0264790 A1 | 11/2006 | Kruijsen et al. |
| 2007/0021842 A1 | 1/2007 | Oddsson et al. |
| 2007/0038168 A1 | 2/2007 | Turrini et al. |
| 2007/0083136 A1 * | 4/2007 | Einarsson ................ 602/26 |
| 2007/0232972 A1 | 10/2007 | Martinez |

FOREIGN PATENT DOCUMENTS

| | | |
|---|---|---|
| EP | 0 931 525 A1 | 7/1999 |
| EP | 1714623 A2 | 10/2006 |
| GB | 2436799 A | 10/2007 |
| WO | 2006/088466 A1 | 8/2006 |

* cited by examiner

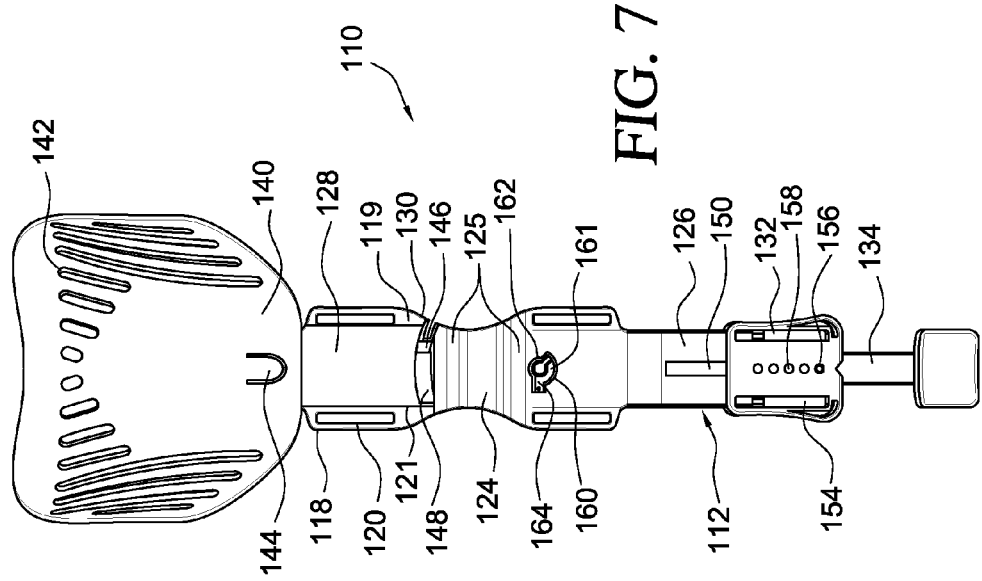
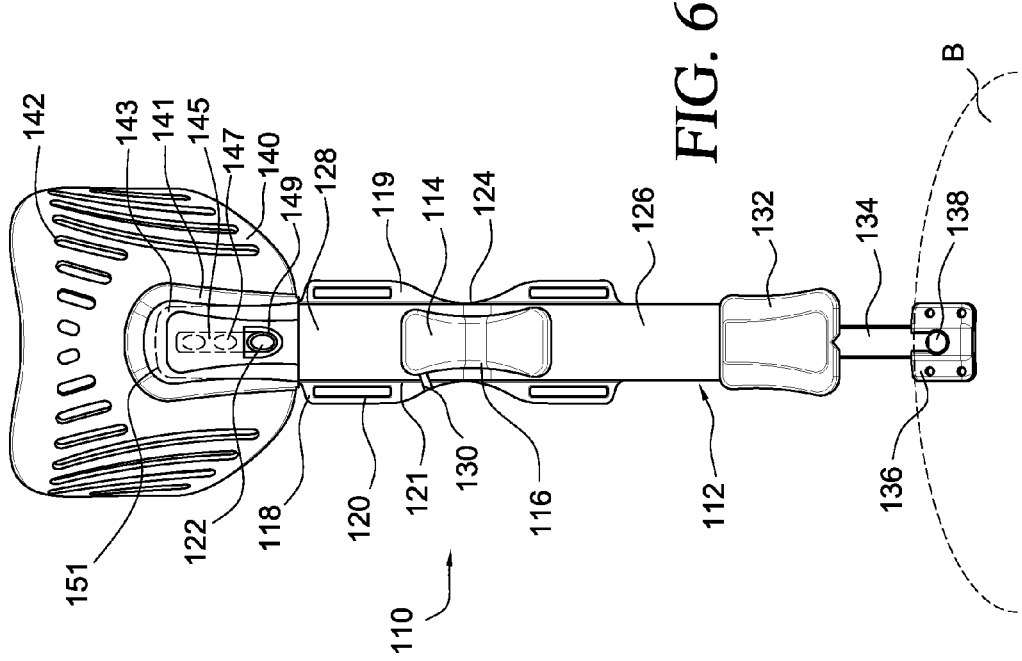

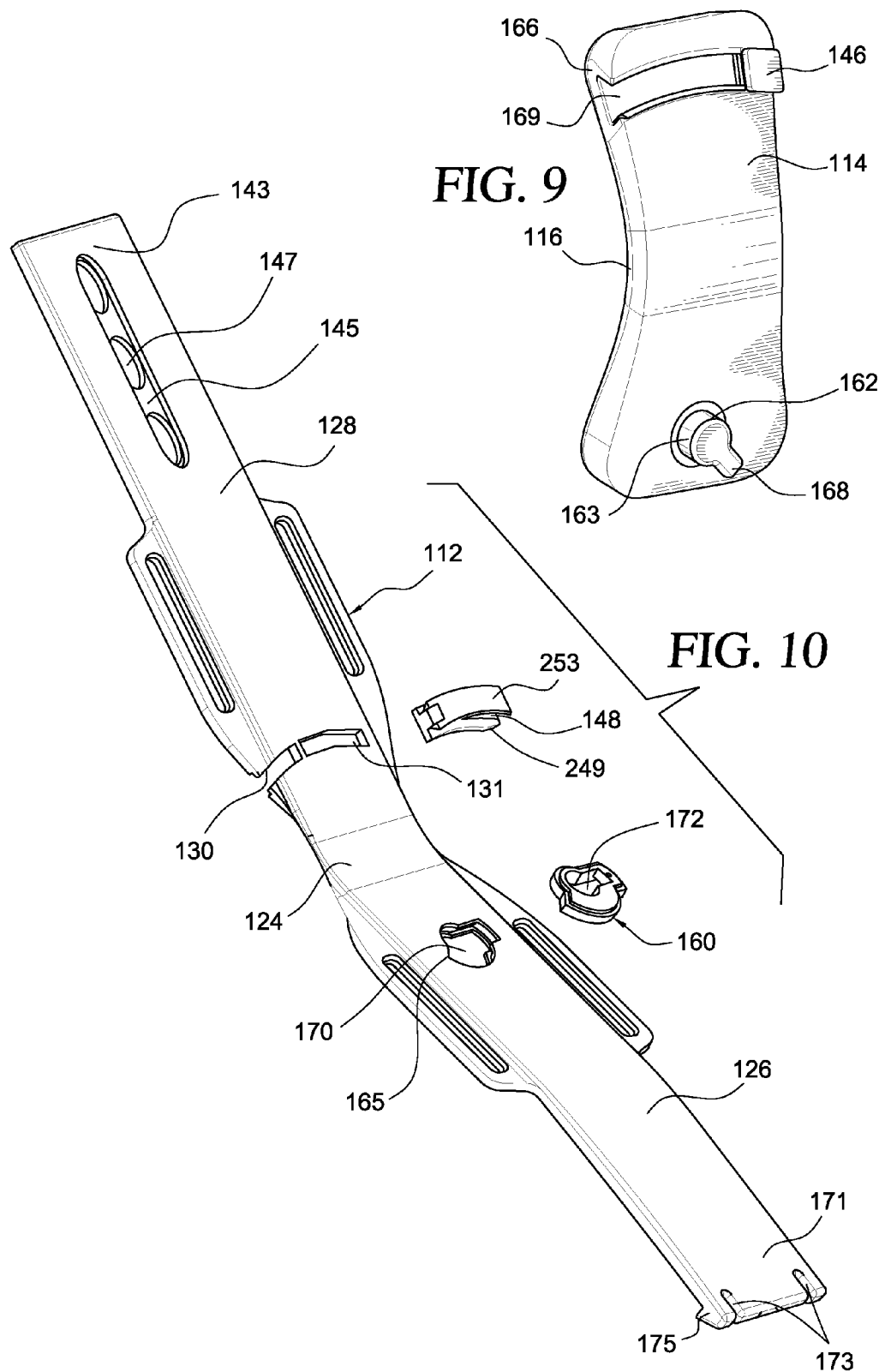

LEG SUPPORT

CROSS-REFERENCE TO RELATED APPLICATIONS

This application claims the benefit of priority of U.S. provisional application No. 61/071,718 filed on May 14, 2008 and U.S. provisional application No. 61/119,480 filed on Dec. 3, 2008.

FIELD OF THE INVENTION

The invention pertains to a leg support for providing force distribution and joint unloading, and more particularly to a leg support having a bendable and resilient portion arranged for being secured along a posterior leg and generally aligned along a medial-lateral plane of the leg.

BACKGROUND

While many known solutions exist for distributing forces and unloading a knee joint, such solutions are often cumbersome, complicated and obtrusive to activities. Some solutions are found in the form of elaborate braces and supports which attempt to compensate the leg of a wearer by providing a series of springs and shock absorbers to assist the wearer during activities. Use of such braces and supports are often frowned upon by the public or are undesirable to wear due to their inherent complexity, size and geometrical configuration, cost, and unaesthetic appearance.

While may braces and supports are effective at distributing forces and unloading a knee joint during physical activities, they can be uncomfortable to wear due to the elaborate and complex mechanics and corresponding elements, and do not provide much convenience for modification or deactivation when still worn but not effectively in use.

Accordingly, there exists the need to provide a leg support which distributes forces and unloads a knee joint while permitting easy use, a streamlined appearance, and a lightweight construction without interfering or serving as an impediment to physical activities.

SUMMARY

In accordance with embodiments of the invention, a leg support is provided and adapted to be secured to a leg. The leg support includes an elongate strut having first and second segments defining a flexible segment located therebetween, and a resilient device releasably secured to the strut. The resilient device corresponds to the flexible strut segment and bending of the support at the knee occurs at the flexible strut segment with the resilient device permitting bending of the leg but resiliently returning the leg to an upright configuration. The combination of the bendable strut and the resilient device permits distribution of forces exerted by the knee joint to the thigh, calf and the footwear upon which the strut is connected so as to unload a knee during physical activities.

A leg support may be worn on each of the wearer's legs thereby providing the necessary distribution of forces required for certain physical activities such as in skiing. When skiing, the footwear is a ski boot upon which the strut is coupled to via a coupling device and an attachment device which accommodates movement of the leg (i.e., varus-valgus movement, and pistoning between flexion and extension).

A variety of different embodiments of the resilient device are embraced by the invention including resilient inserts that are removable from the posterior strut or those which have means for disengaging the resilient device from resisting bending of the middle segment of the posterior strut. Alternatively, arrangements include using multiple resilient inserts or spring configurations which provide different resistance for different sides of the leg (e.g., medial and lateral).

The features, aspects, and advantages of the present invention will become better understood with regard to the following description, appended claims, and accompanying drawings.

BRIEF DESCRIPTION OF THE DRAWINGS

FIG. 6 is a front elevational view showing another embodiment of a leg support.

FIG. 7 is a rear elevational view showing the leg support of FIG. 6.

FIG. 9 is a perspective view showing the resilient device according to FIG. 6.

FIG. 10 is an exploded perspective view showing the posterior strut of FIG. 6.

DETAILED DESCRIPTION OF VARIOUS EMBODIMENTS

A. Overview

Figure 1:
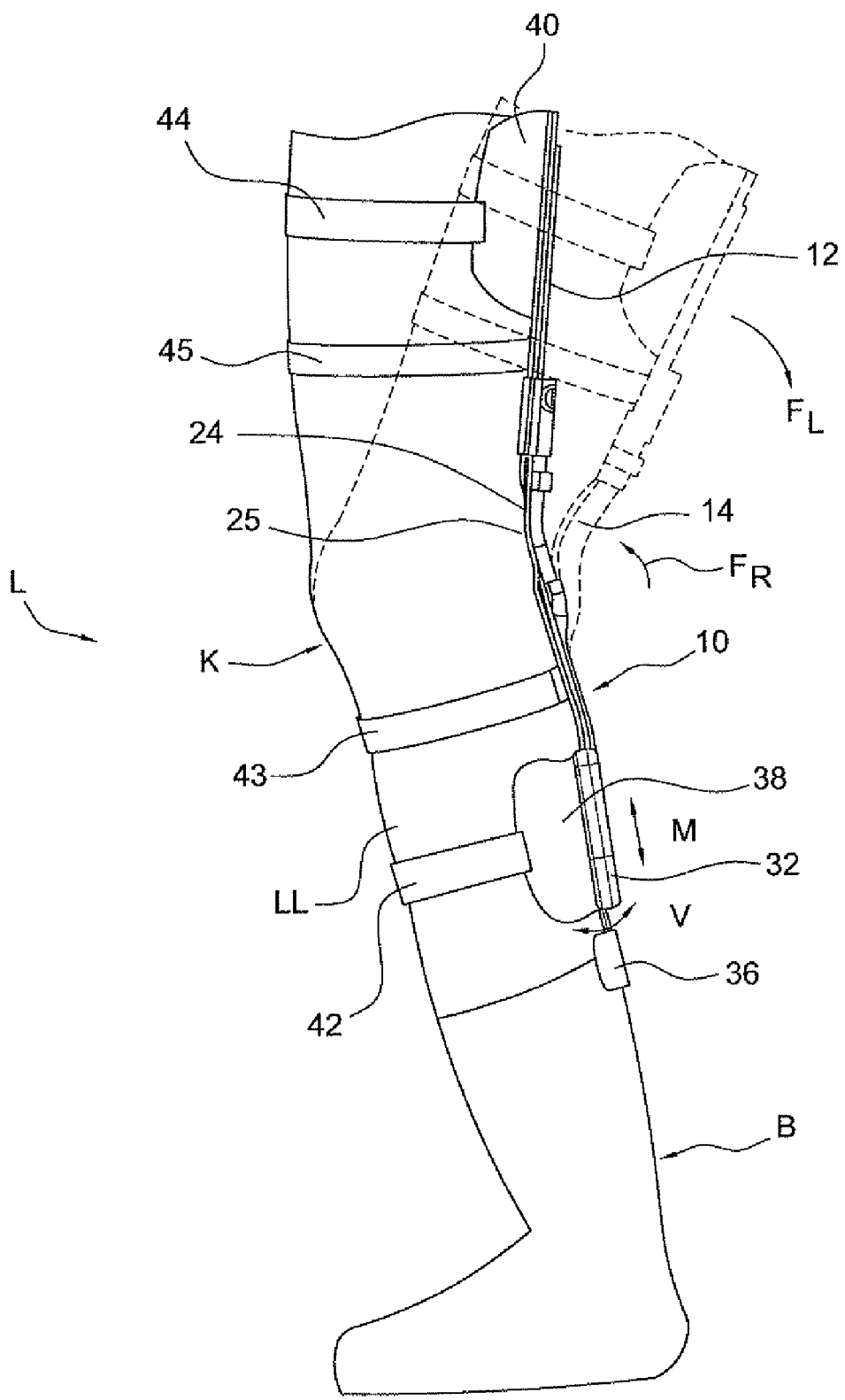
FIG. 1 is a side elevational view showing the leg support on a leg of a wearer and connected to a ski boot.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

B. Environment and Context of Embodiments

Numerous leg support embodiments and components for use therewith are described herein, with particular focus given to supports and components directed to the knee joint and surrounding areas. The leg support embodiments may serve in protective, preventative or remedial capacities. While the leg support is described within the context of preferred embodiments that are directed to supporting and unloading a knee joint, many of the features described herein may be extended to other supports and components that bear or secure other joints and body parts, such as the wrist, elbow, shoulder, ankle and neck.

The leg support embodiments and components for use therewith may be dimensioned to accommodate different types, shapes and sizes of human joints and appendages. These embodiments may be modified to orient principal forces exerted by the leg.

As is well understood, the primary movements of the knee comprise flexion, i.e., rearward rotational movement of the tibia relative to the femur, and extension, i.e., forward rotational movement of the tibia relative to the femur.

For explanatory purposes, each leg support or component thereof described herein may be divided into sections which are denoted by general anatomical terms for the human body. Such anatomical terms are provided to distinguish various elements of the leg support embodiments from one another, but which are not to be considered to limit the scope of the invention.

Each of these terms is used in reference to a human leg, by way of example, which is divided in similar sections with a proximal-distal plane generally extending along the meniscus of the knee between the femur and tibia. The terms "proximal" and "distal" generally refer to locations of the support that correspond to the location of leg relative to the point of attachment of the leg to the body. The terms "upper" and "lower" may be used in combination with "proximal" and "distal" to connote gradations in location of "proximal" and "distal." The location at where the support corresponds to the knee joint is used herein to generally delimit the proximal and distal sections of the support.

The embodiments of the leg support can also be considered to fall within "anterior" and "posterior" sections by an anterior-posterior plane. The anterior-posterior plane generally corresponds to the coronal or frontal plane of a human leg which lies along the central longitudinal axis of a body. A posterior side or element is therefore located behind this anterior-posterior plane, whereas an anterior side or element is located in front of the anterior-posterior plane.

The terms "inwardly" or "inner" commonly used herein to distinguish the side of the leg support that may be directed to the posterior side of the support and specifically adjacent to the leg of the wearer of the support. On the other hand, the term "outwardly" or "outer" are used to denote the side of the support that is opposite to the inwardly side.

The terms "medial" and "lateral" are relative terms that are generally understood as indicating location near the midsaggital plane or midline. Therefore, elements that are located near the midline are referred to as "medial" and those elements that are further from the midline are considered to be "lateral." The term "central" is used to denote the area along the midline including portions of the medial and lateral regions.

The terms "rigid" and "flexible" are repeatedly used herein to distinguish characteristics of portions of the support. The term "rigid" is intended to denote that an element of the support is generally devoid of flexibility. Within the context of support members that are "rigid," it is intended to indicate that they may break if bent with sufficient force. On the other hand, the term "flexible" is intended to denote that features are capable of repeated bending. The term "resilient" is used to qualify such flexible features as generally returning to the initially molded shape without permanent deformation.

The anatomical and characteristic terms described herein are not intended to detract from the normal understanding of such terms as readily understood by one of ordinary skill in the art of orthotics. Moreover, the elements of the embodiments described herein are intended to embrace embodiments that generally correspond to the aforementioned anatomical sections. In other words, it is understood that the elements of the support embodiments described herein may deviate from falling exactly within the confines of the aforementioned anatomical sections.

C. Various Embodiments of the Leg Support and Components for Use Therewith

In observing FIG. 1, an embodiment of the leg support is shown and designated 10. For explanation purposes, the leg support 10 is mounted on a leg L of a wearer having an upper leg portion UL, a lower leg portion LL and a knee K. The wearer is shown wearing a footwear in the form of a ski boot B.

The leg support 10 includes a generally elongate strut 12 which is secured on the posterior side of the leg generally along the midline of the leg L. The midline is considered to generally fall along a medial-lateral plane dividing the leg. Lower and upper leg cuffs 38, 40 connect to the strut 12 and embrace portions of the leg with the strut 12 having openings 56 for connection with the upper let cuff 40. Particularly, the lower cuff 38 extends about only the posterior side of the lower leg LL and reaches into both the medial and lateral sides of the leg. Likewise, the upper cuff is shown as only extends about the posterior side of the upper leg UL and into both the medial and lateral sides of the leg.

Suitable first lower and upper strapping devices 42, 44, are secured to the lower and upper cuffs 38, 40, and circumferentially extend about the leg L. An example of cuffs that may be used herewith are found in co-pending U.S. application Ser. No. 11/035,133, incorporated herein by reference and owned by the assignee of this application. Additionally, second lower and upper strapping devices 43, 45 are adjacently located above and below the knee K to secure the brace at such locations relative to the leg L. These straps assist in maintaining close approximation of the brace to the knee as the knee moves between flexion and extension.

A particular advantage to this embodiment is that there is limited or no intrusion of the lower and upper cuffs along the medial and lateral sides of the leg near the anterior-posterior plane. This arrangement provides a support which minimizes the possibility of the support impacting the wearer's other leg during use, such as when the wearer is skiing and experiences bumps and vibrations. The arrangement also mitigates the risk of the cuffs catching on clothing, clattering with ski poles or other supports, or a support worn on the other leg.

Because of the streamlined profile of the leg support, the wearer can wear the leg support inside of pants thereby allowing the brace to be worn without a noticeable appearance. Despite the illustrated construction and placement of the cuffs, the leg support is not limited to the configuration shown herein, and it is envisioned that the cuffs may embrace significantly more portions of the leg than that shown herein, such as along both anterior and posterior portions of the leg.

The leg support 10 includes a resilient device 14 which is secured to the strut 12 at a flexible middle segment 24 thereof. A retainer 20 holds at least part of the resilient device 14 to the strut 12. The middle segment 24 and the resilient device 14 are each formed with a contour having a bend 25 corresponding to one another at a location along the posterior side of the knee K.

The leg support 10 is secured to the boot B by way of a coupling device 36 mounted on the boot B. In accordance with this embodiment, the strut 10 is pivotally mounted at a single point to the boot B so as to permit varus/valgus adjustment V of the leg support relative to the boot B. This permits the wearer to lean in either right or left directions when wearing the leg support.

The leg support also has an attachment device 32 which connects the strut 12 to the coupling device 36. The attachment device 32 is slidably connected to the strut 12 and is fixably connected to the coupling device 36. The attachment device 32 permits pistoning of the strut 12 in direction M relative to the coupling device 36 and footwear, thereby allowing the lower and upper cuffs 38, 40 to remain in place on the leg without movement.

In use, as the knee K bends, the force FL of the upper leg UL is exerted to the resilient device 14 which resists the force FL with force FR. The resilient device 14 absorbs the force FL by distributing it away from the knee to the upper leg UL, lower leg LL and the ski boot B.

Figure 4:
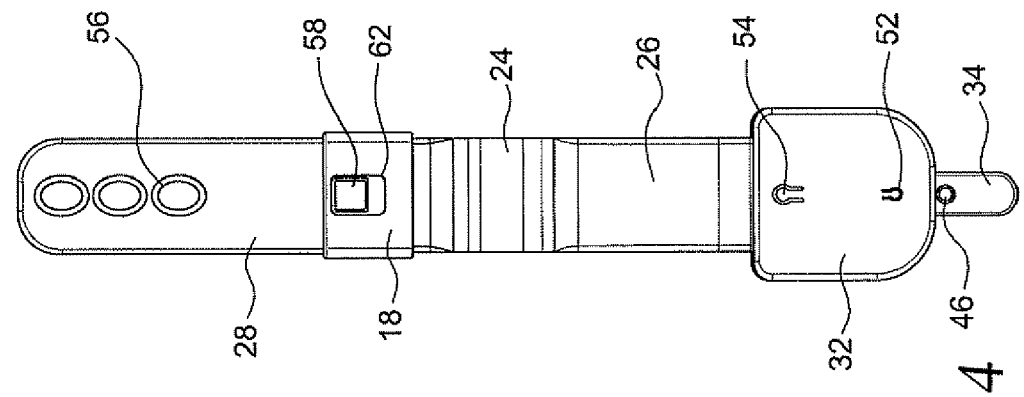
FIG. 4 is a rear elevational view showing the leg support of FIG. 2.
Figure 3:
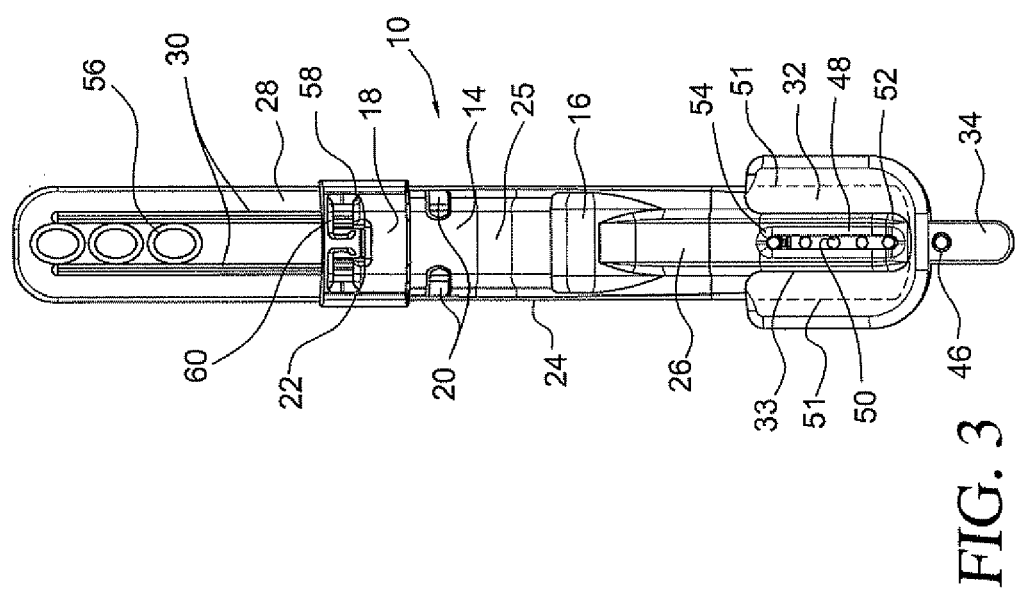
FIG. 3 is a front elevational view showing the leg support of FIG. 2.
Figure 2:
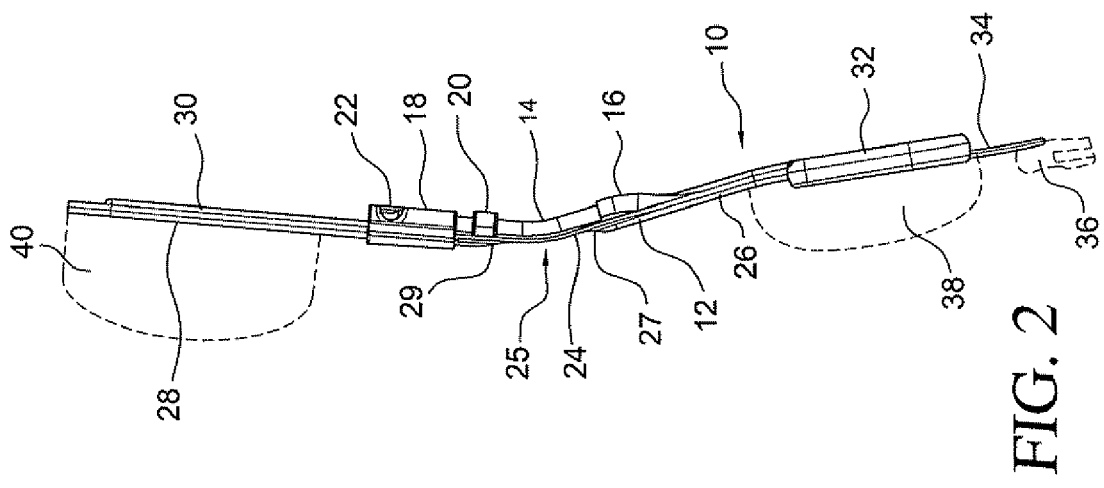
FIG. 2 is a detailed side elevational view showing the leg support of FIG. 1.

In turning to FIGS. 2-4, a detailed description of the leg support 10 is provided. The strut 12 is primarily divided into a lower leg or first segment 26, an upper leg or second segment 28, with the middle segment 24 located therebetween. The middle segment 24 has a thickness that is reduced relative to the lower and upper leg segments 26, 28. The thickness of the lower and upper leg segments 26, 28, tapers at lower and upper transitions 27, 29, located on an inner or first surface of the strut 12 (side adjacent the leg of the wearer) and which serve as first and second end portions, respectively, to the middle segment 24.

Because the middle segment 24 has a reduced thickness, preferably a substantially thin, plate-like form, the strut 12 is substantially flexible along the middle segment 24. Further, the bend 25 further facilitates bending of the strut 12 along the middle segment 24 since the contour of the middle segment 24 is arranged such that it is anatomically shaped to correspond to the flexion or bending position of the knee. As depicted in FIG. 1 and FIG. 2, the strut 12 is formed so as to anatomically correspond to the leg and knee in the extension or upright position of the leg L and knee K.

The strut is preferably formed from a material that permits the middle segment 24 to be resilient, thereby generally returning to its pre-formed shape after a load exerted on the middle segment has been released. Preferably, this shape corresponds to an upright configuration or extension position of a leg. Thus, while the middle segment may be flexible, it does not undergo permanent deformation upon bending. Moreover, because the lower and upper leg segments have a greater thickness, they preferably have rigid or semi-rigid properties in order to stably secure to the leg and withstand loads exerted thereon.

The strut is preferably a monolithic and continuous single injection molded piece. A preferable material that may be used to form the strut is a polyamide such as the commercial product ULTRAMID sold by BASF. Other materials may be used to form the strut include but are not limited to carbon-fiber reinforced resins, glass-fiber or glass reinforced resins and polymers, and other polymeric materials. This monolithic injection-molded strut is particularly advantageous in that it mitigates the need for any fasteners or other components that are used in conventional braces.

Suitable locking elements, protrusions and recesses may be formed on the strut which connect to other similarly correspondingly molded components, such as those described below, so as to trim down weight, improve coverage on the anatomy of the wearer, reduce manufacturing costs, simplify adjustment of the leg support, and provide a support easy to use for the wearer.

The strut may be reinforced with suitable elements such as by structural material inserts which have greater rigidity than the remainder of the material forming the strut. Alternatively, reinforcement ribs and other structural arrangements may be used to strengthen areas of the strut.

According to this embodiment, the resilient device is a resilient insert that is preferably formed from a monolithic, continuous single-piece thermoplastic coopolyester elastomer (TPE). A preferred material for forming the insert, preferably by injection molding, is RITEFLEX sold by Ticona. Other materials may be used but are not limited to rubbers and other polymeric materials. Preferably, the material and geometrical configuration of the insert is selected so that it is resilient to bending loading. The resilient insert may be reinforced with wires, bands, composite plates or bars, or other suitable reinforcing elements to facilitate both bending and resiliency to a molded configuration.

This insert has a thickness which is substantially greater than the middle segment, and width generally corresponding to or less than the width of the middle segment. The length of the insert, however, is longer than the length of the middle segment, thereby enabling the insert to be secured to the strut along the lower and upper leg segments. The insert is contoured in the same manner as the middle segment of the strut, and may have the bend which facilitates and directs bending of the insert in its preconfigured shape.

The insert may be tailored according to a variety of different material properties such as stiffness, compression, and resiliency, or geometrical shapes (i.e., thickness and width). Thus, a wearer may be able to select from a variety of different inserts for use with the strut in accordance with certain requirements and preferences specific to the wearer, thereby adding to the versatility of the leg support to accommodate a variety of different wearers.

The lower leg segment 26 forms a lower mount 16 which is configured for receiving a lower or first end portion of the insert 14. The lower mount 16 is configured so that the first end of the insert 14 snugly fits within the lower mount 16.

The upper leg segment 28 defines parallel elongate ribs 30 that extend generally along an outer or second surface of the strut 12. An upper mount 18 is connected to the upper leg segment 28 and has corresponding grooves 60 which permit the upper mount 18 to be slidable along the ribs 30. The upper leg segment 28 defines a resilient tab 58 which extends from the second surface of the strut and protrudes outwardly therefrom. The upper mount 18 defines a release button 22 having a detent which resiliently extends from the upper mount 18 towards the tab 58 so as to effectively lock movement of the upper mount 18 relative to the upper leg segment 28. The upper mount 18 defines an opening 62 located along the first surface thereof which permits deflection of the tab 58 so as to allow disengagement of the upper mount 18 from the tab 58.

Figure 5:
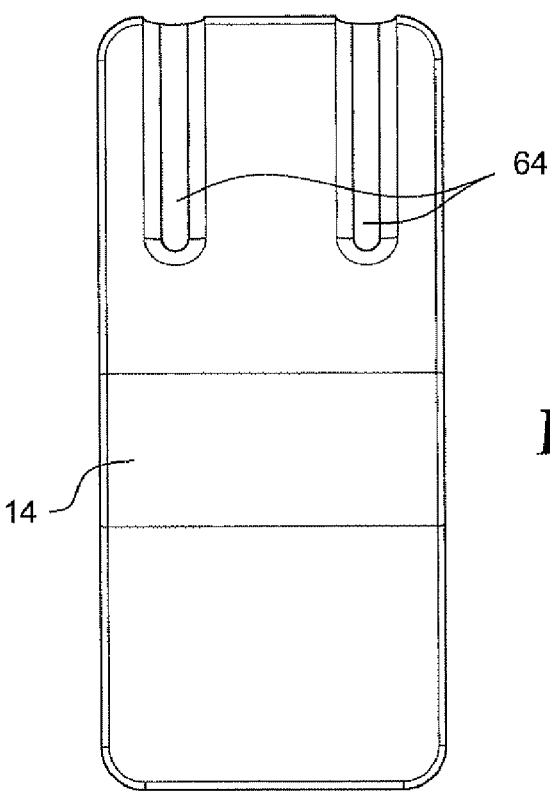
FIG. 5 is a rear elevational view showing the resilient insert according to FIG. 2.

The upper mount 18 is configured to receive the second end portion of the insert 14 so as to secure and clamp the insert 14 at the second end portion thereof. As shown in FIG. 5, the insert 14 forms grooves 64 which correspond to the ribs 30, thereby further securing the insert 14 to the strut 12. Thus, the lower and upper mounts 16, 18 combine to pin down both the first and second end portions thereof relative to the strut 12. Securing retaining tabs 22 may additionally be used which are located above the bend 25 of the strut 12 and the insert 14. It will be noted, however, that it is preferable that the insert merely rests adjacent the second surface of the middle segment so as to facilitate combined bending of the strut and the insert.

Figure 5A:
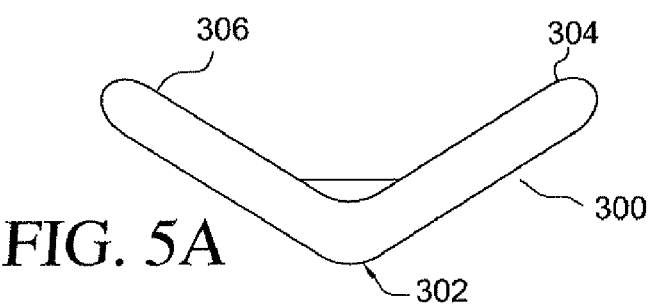
FIG. 5A is an elevational view showing an embodiment of a resilient insert.
Figures 5B, 5C:
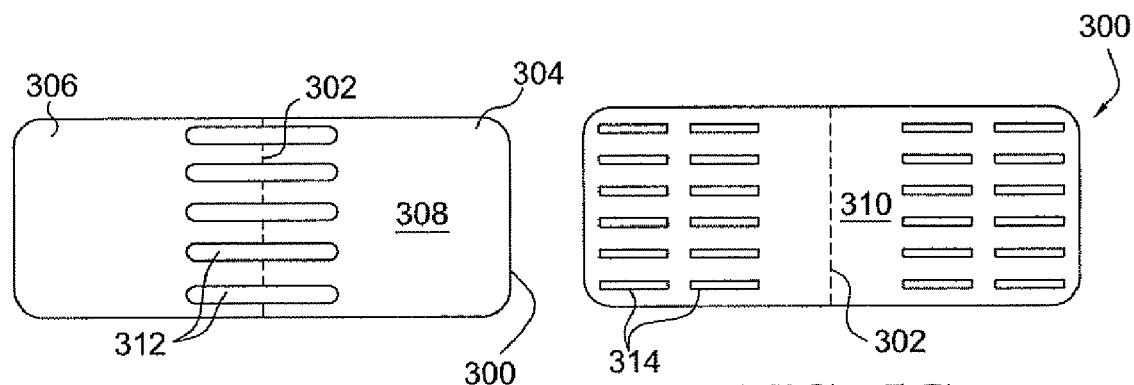
FIG. 5B is a top plan view showing the embodiment of FIG. 5A.
FIG. 5C is a bottom plan view showing the embodiment of FIG. 5A.

FIGS. 5A-5C illustrate an alternative embodiment of the resilient device. According to these drawings, a monolithic resilient insert 300 is formed with an anatomically contoured bend region 302 and is arranged to fit in a similarly anatomically contoured posterior strut. The insert 300 defines first and second ends 304, 306 which are preferably but not limited to being equidistant from the bend region 302.

The insert 300 defines bolsters 312 located on a first or outside surface 308 directed away from the leg. These bolsters 312 reinforce the area of the bend region so as to provide the insert with greater strength and stiffness at the bend region 312 upon bending. In order to reduce weight of the insert, the insert defines a plurality of recesses 314 at areas outside the bend region 312, as shown from a second surface 310. It will be noted that the insert is not limited to the bolsters and recesses depicted herein, and a variety of methods may be used to provide areas of increased strength and reduced weight. Moreover, the insert may not be monolithic and strengthening means such as ribs, springs or other means may be applied to the insert to improve the strength and stiffness at the bend region.

Figures 5D, 5E:
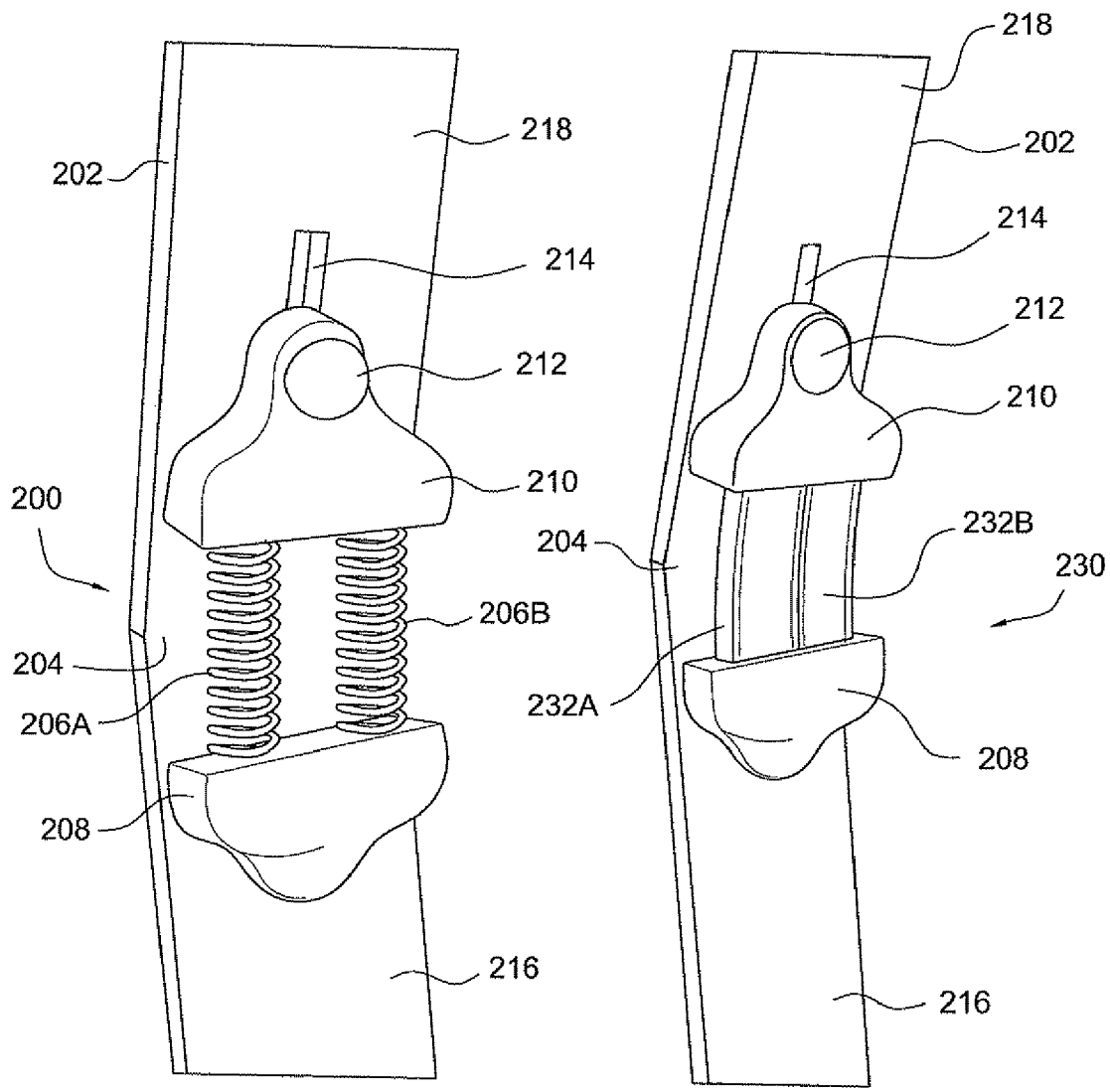
FIG. 5D is a perspective sectional view showing another embodiment of the leg support.
FIG. 5E is a perspective sectional view showing another embodiment of the leg support.

In observing FIGS. 5D and 5E, additional embodiments of the resilient device may be used in combination with different arrangements of the strut. As illustrated in FIG. 5D, the resilient device 200 is provided on a variation of a strut 202. In this embodiment, the strut 202 does not have a transitional or reduced thickness; however a bend 204 is formed much in the same manner as described above in connection with other embodiments. Lower and upper segments 216, 218 are defined below and above the bend 204 such that the upper segment 218 is flexible relative to the lower segment 216 at the bend 204.

The resilient device 200 comprises a base 208 fixably secured below the bend 204, and a cap 210 slidably mounted on the middle segment 202. The cap 210 includes a pin 212 which is slidably attached within an elongate slot 214 permitting the cap 210 to slide relative to the base 208 and the strut 202. Parallel compression springs 206A, 206B are connected to and span between the base 208 and the cap 210. The resilient device 200 is arranged such that as the upper strut segment 218 flexes at the bend 204 relative to the lower strut segment 216, the compression springs 206A, 206B resist bending of the leg.

FIG. 5E presents another embodiment with a resilient device 230 arranged similarly to the embodiment of FIG. 5D, however resilient cylindrical inserts 232A, 232B are used between the base 208 and cap 210. These cylindrical inserts 232A, 232B resist movement of the upper segment 218 relative to the lower segment 216.

The compression springs 206A, 206B, and the cylindrical inserts 232A, 232B may be arranged so that they have different stiffnesses. For example, the compression spring or cylindrical insert corresponding to the lateral side of the leg may be stiffer than the compression spring or cylindrical insert corresponding to the medial side of the leg. This arrangement is provided to resist more movement on the lateral side of the leg than the medial side of the leg since it has been found in certain activities that the lateral side of the leg undergoes more stress and strain than the medial side.

Returning to the embodiment of FIGS. 1-4, both the lower and upper leg segments 26, 28, provide means for adjustment of the cuffs 38, 40, along the strut 12. In observing the lower leg segment 26, an attachment device 32 slidably secures onto the end portion of the lower leg segment 26. The attachment device 32 defines internal grooves 51 (shown in dashed lines) configured to receive the lower leg segment 26. The lower leg segment 26 in turn defines a channel 48 through which a pin 54 of the attachment device 32 extends thereby providing a sliding arrangement between the lower leg segment 26 and the attachment device 32. The attachment device 32 having a opening 33 showing part of the extension 34.

The sliding arrangement results in the attachment device 32 sliding relative to the lower leg segment 26 to mitigate pistoning of the strut 12 itself as the knee goes between extension and flexion. This arrangement effectively eliminates pistoning of the thigh shell, and by way of the straps and cuffs, allows the strut to remain in the same place on the leg as the knee goes between extension and flexion thereby providing uniform and constant support to the wearer.

It will be noted that in combination with the aforementioned embodiment of the sliding arrangement, a variation of the sliding arrangement may include a spring element in combination with the pin and the channel. Such a spring may include a compression spring of known types which assist in returning or maintaining the leg into an extension position.

An elongate extension 34 is adjustably secured to both the lower leg segment 26 and the attachment device 32. The extension 34 defines a series of apertures 50 located at a first end portion and middle portion thereof along its longitudinal length of which the apertures 50 are engageable with a resilient button 52 of the attachment device 32. The adjustability of the button 52 relative to any one of the apertures 50 allows for the strut 12 to be adjusted in length relative to the footwear upon which it may be attached, as in the boot of FIG. 1. The extension 34 also defines a hole 46 generally located at a second end portion thereof which is adapted to engage structure on the coupling device 36 used to secure the support to footwear.

Figure 8:
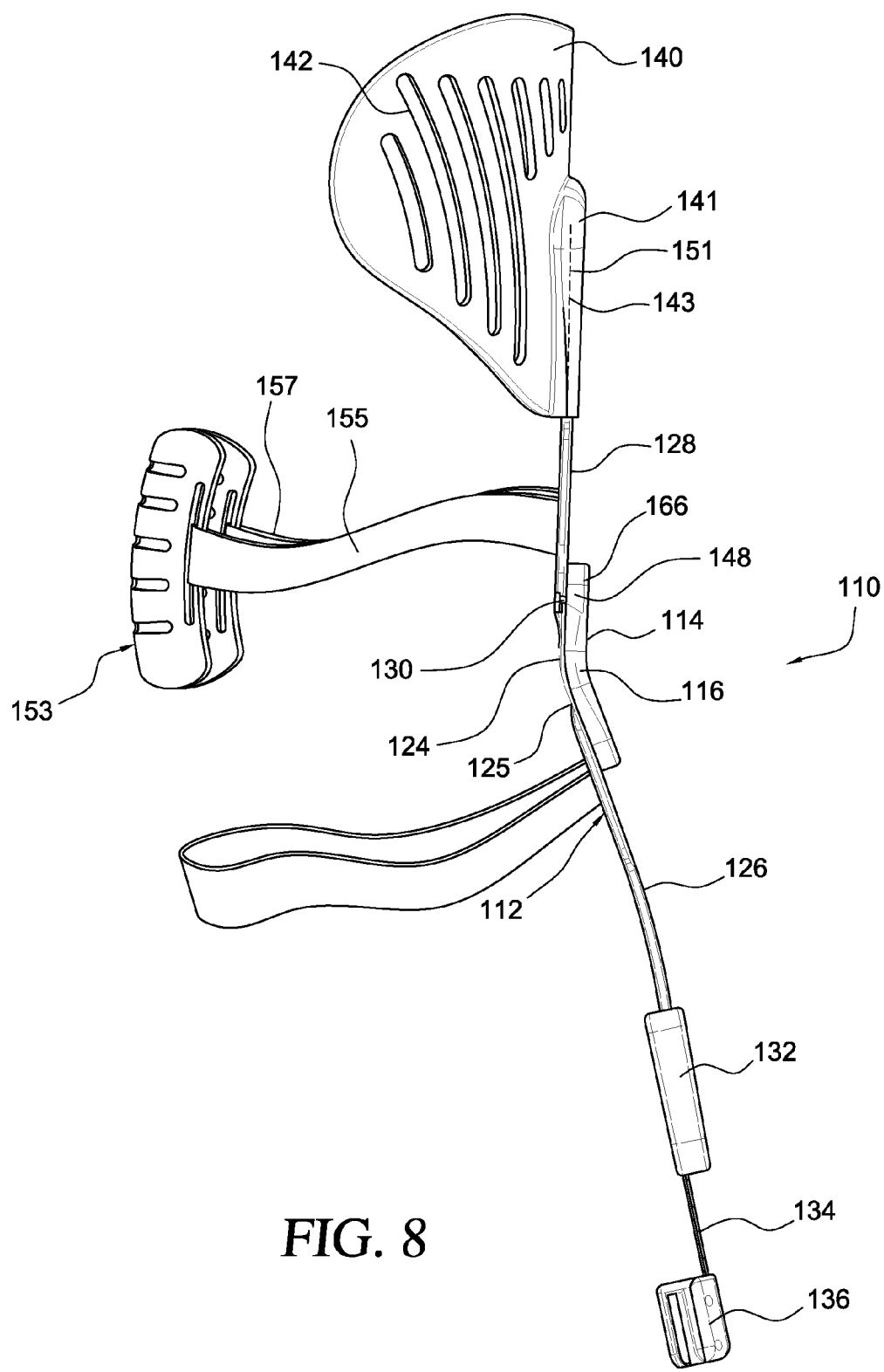
FIG. 8 is a side elevational view showing the leg support of FIG. 6.

FIGS. 6-8 depict another embodiment of the leg support 110 in accordance with the invention. The leg support includes a posterior strut 112, and a resilient device or insert 114 having contoured edges 116 and being attached to the posterior strut 112.

The posterior strut 112 defines a generally flexible middle segment 124, and elongate lower and upper leg segments 126, 128. The lower and upper leg segments 126, 128 are substantially more rigid than the middle segment 124. The middle segment 124 defines a reduced thickness region relative to the lower and upper leg segments, and further defines a contour having a bend 125, much in the manner in accordance with the embodiment of FIG. 1.

The posterior strut 112 forms strapping elements 118 defining openings 120 for attachment of an appropriate strap (exemplified in FIG. 8). The strapping elements 118 are integrally formed with the lower and upper leg segments 126, 128 via flared portions 119 which generally extend transversely relative to the lower and upper leg segments. These flared portions 119 have a reduced thickness relative to the lower and upper leg segments and have a tapered contour in order to distribute forces onto the leg exerted by the straps. The flared portions generally terminate near or at the middle segment 124 so as to permit ample adjustment of the resilient insert 114.

The strapping elements 118 may also include a living hinge 121 effectively dividing the strapping elements from the lower and upper leg segments. The living hinge 121 permits the strapping elements to bend relative to the more rigid lower and upper leg segments so as to better accommodate the shape of a leg when straps are used to secure the support onto leg.

In accordance with the embodiment of FIGS. 6-8, a posterior thigh shell or cuff 140 adjustably connects at a first end portion 141 of the upper leg segment 128. The shell 140 is adapted to accommodate the contours of a leg and defines a plurality of openings 142 to greater increase ventilation and breathability on the leg. Suitable padding may be employed in combination with the shell such as padding described in U.S. application Ser. No. 11/723,604, incorporated herein by reference.

The shell 140 is adjustably secured to the upper leg segment 128 via a button tab 122 integrally formed therewith and biased from the shell towards the upper leg segment 128. As shown in FIG. 6 and likewise FIG. 10, the first end portion 141 of the upper leg segment 128 defines an elongate recessed portion 145 having a series of holes 147 adapted to receive and lock with the button tab 122. This provides for height adjustment of the shell 140 along the upper leg segment 128.

In the embodiment of FIG. 6, the button tab 122 extends from the rear side of the shell 140 and is exposed via an opening 149 on the front side of the leg support. In order to adjust the height, one must press the button tab 122 from the front side of the leg support, and adjust the height of the shell accordingly.

The shell 140 includes a housing section 143 which covers at least some of the first end portion 143 including the recessed portion 145 and the holes 147, and permits adjustment of the shell 140, while exposing the button tab 122. The upper leg segment 128 closely fits within a cavity 151 (depicted with dashed lines showing the internal periphery thereof) of the housing section 143 and slides relative therewith so as to permit adjustment of the shell relative to the housing section. The housing section 143 protrudes outwardly from the shell so as to form the cavity 151.

In addition to the posterior thigh shell 140, an anterior thigh shell 153 may be provided which secures to the posterior strut 112 via strapping devices 155 and 157. The anterior thigh shell 153 stabilizes the leg support relative to the anterior aspect of leg, and effectively counteracts with the shell 140.

In accordance with the embodiment of FIG. 6, a detailed depiction of the resilient insert 114 and the posterior strut 112 are shown in FIGS. 9 and 10. The resilient insert 114 includes a locking tab 146 and an elongate slide channel 169. The locking tab 146 and slide channel 169 may be formed from a single piece forming a coupling part 166 which has a greater hardness than the material used to form the remainder of the resilient insert. For example, the coupling part 166 is molded into the resilient insert 114, and effectively impregnated into the material of the resilient insert 114. The locking tab 146 is arranged to couple in a first slot 130 defined along the edge of the middle segment 124. The locking tab 146 is similarly formed to slide and lock with the first slot 130.

A stanchion 148 is secured by a second slot 131 formed by the middle segment, and defines a lower flange 249 and a tapered head 253. The lower flange 249 is retained by the rear side of the middle segment and the tapered head 253 protrudes outwardly from the front side of the middle segment 124. The tapered head 253 has a shape corresponding to the slide channel 169 thereby permitting the stanchion 148 to slide therein.

The resilient insert 114 also includes a locking dial 162 having a post 163 with an arm 168 extending from a top portion thereof. Preferably, the locking dial 162 is impregnated into the resilient insert 114, with the post 163 extending outwardly therefrom.

The lower leg segment 126 forms an opening 170 arranged to receive a plate 160 which secures therewithin. The plate 160 defines a passage 172 that is sized and configured to accommodate the locking dial 162, thereby permitting the post 163 and the arm 168 to extend therethrough.

The plate 160 defines a recess 161 (shown in FIG. 7) on the rear side thereof which has a depth generally corresponding to the thickness of the extension 168 thereby permitting the arm 168 to rest within the recess 161. Because the locking dial 162 extends through the passage 172, the resilient insert 114 can rotate relative to the posterior strut 112.

The periphery of the opening 170 forms a stop surface 165 which prevents rotation of the resilient insert 114 in a first direction. A detent 164 is removably secured to or formed on the rear side of the insert 114 so as to prevent rotation of the resilient insert in a second direction.

As the resilient insert 114 rotates in a first direction relative to the posterior strut 112, the head 153 of lower flange 249 engages the slide channel 169 of the coupling part 166 and the locking tab 146 engages the first slot 130 so as to lock the resilient insert 114 relative to the posterior strut 112. When placing the resilient insert 114 on posterior strut 112, the detent 164 is removed from the insert 160 so as to permit extension of the dial 162 through the opening 172.

Once the resilient insert 114 is rotated to a certain degree, one may attach the detent (which may be secured accordingly with removable fasteners) so as to prevent detachment of the resilient insert from the posterior strut. In order to place the resilient insert in a fully operational position relative to the posterior strut, the resilient insert is urged in the first direction so that the locking dial engages the stop surface 165.

When it is desired to disengage the resilient insert from operation on the posterior strut, one can rotate the resilient insert from the flanged element and the first slot in the second direction. This disengagement of the resilient insert maintains the resilient insert secured to the posterior strut, but places the resilient insert in a position which does not resist and provide spring back to the posterior strut. In effect, the user can generally freely flex and extend the knee without the impact or resistance caused by the resilient insert.

Figure 11:
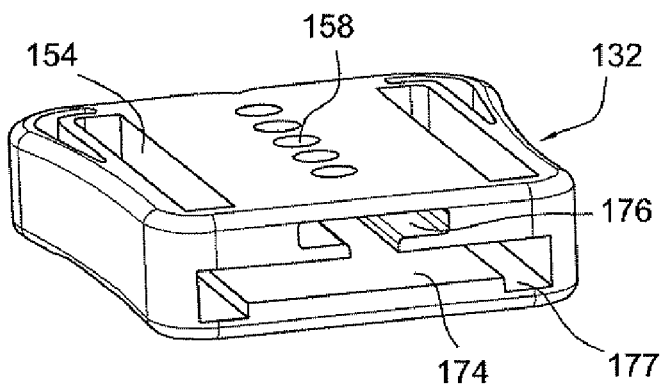
FIG. 11 is a perspective view showing the attachment device of FIG. 6.

In turning to the boot attachment system, FIG. 11 depicts the attachment device 132 which is arranged to receive a lower end portion 171 of the posterior strut 112. The lower end portion 171 defines grooves 173, and locking fingers 175 which resiliently extend from the lower end portion 171 so as to engage the attachment device 132.

The attachment device 132 defines a front slot 174 arranged to receive the lower end portion 171, and further defines side portions 177 which permit the locking fingers 175 to be flexibly received therein. As the lower end portion 171 is inserted into the front slot 176, the locking fingers 175 deflect and subsequently spring back to be slidably engaged within channels 154 formed by the attachment device. The attachment device 132 can effectively slide along channel 150 of the lower segment 126 (as depicted in FIG. 7).

The ability of the attachment device 132 to slide relative to the posterior strut is particularly beneficial, as explained above in connection to the embodiment of FIG. 1, in that the boot attachment system can piston relative to the posterior strut which is effectively fixed in place on the leg. This movement permits the leg support to accommodate movement of the leg as it goes between extension and flexion.

Figure 12:
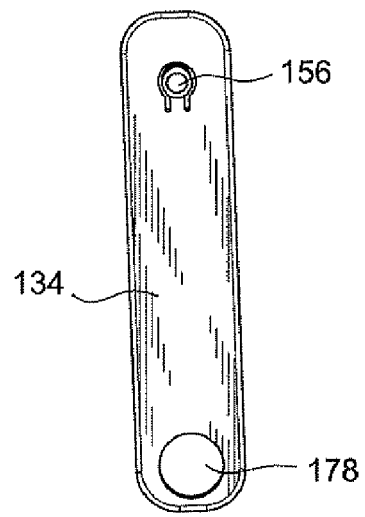
FIG. 12 is an elevational view showing the extension of FIG. 6.

The attachment device 132 also defines a rear slot 176 adapted to receive the extension 134, as depicted in FIG. 12. The attachment device 132 defines a series of apertures 158 arranged along the height of the attachment device 132. The apertures 158 are formed so as to receive a tab 156 resiliently extending from an upper end of the extension 134. When placed in the rear slot 176, the tab 156 is biased towards the rear surface of the attachment device 132, such that the tab 156 is urged into the first aperture 158 located proximate to the entrance of the rear slot 176. The extension 134 may be adjusted relative to the attachment device by pressing the tab 156 out from the first aperture 158 and subsequently adjusted to the appropriate aperture in the series of apertures in order to adjust the distance of the attachment device 132 relative to the coupling device 136.

Figure 13:
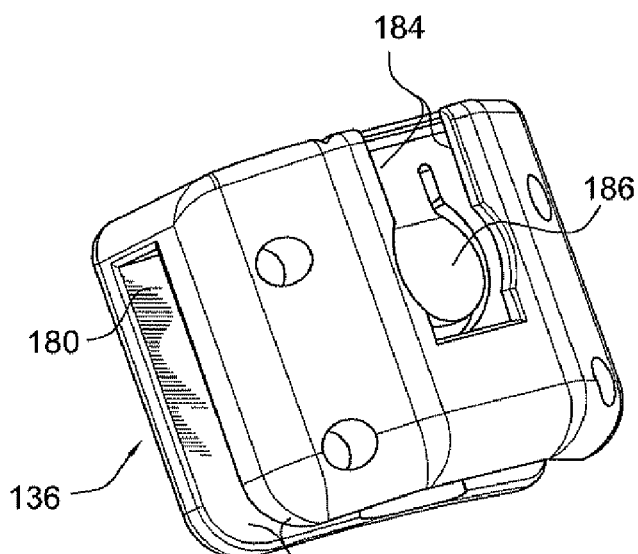
FIG. 13 is a perspective view showing the coupling device in the embodiments of FIGS. 1 and 6.
Figure 14:
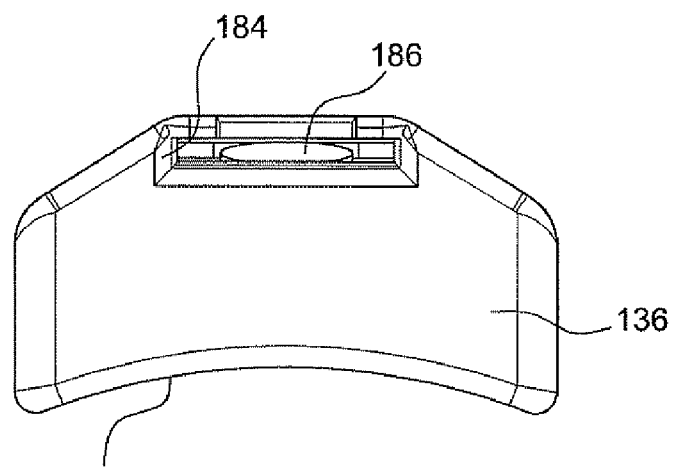
FIG. 14 is a plan view showing the coupling device of FIG. 13.

As illustrated in FIGS. 13 and 14, an embodiment of the coupling device 136 is shown as having a clamping member 180 which is adapted to secure to an edge of a ski boot, as depicted in FIG. 1. The clamping member 180 has arms 182 which may be biased towards one another so as to assure that the clamping member 180 secures to the boot. The clamping member 180 has an inner or first surface having a contour 190 generally corresponding to the contour of a boot. The clamping member 180 also has an outer or second surface which defines opposed grooves 184 adapted to receive the extension 134 therein.

The clamping member 180 has a resilient button 186 located between the grooves 184 which is arranged for engaging a hole 178 formed at a lower end of the extension 134. The hole 178 snap fits to the resilient button 186 so as to effectively encircle at least a portion of the button. This coupling between the clamping member 180 and the extension 134 may be arranged to permit some play of the extension 134 relative to the clamping member 180 and hence the boot, thereby accommodating varus/valgus movement of the posterior strut 112 relative to the boot.

According to one variation of the coupling device, the grooves may be sized in a manner such that the extension closely fits therein thereby preventing any movement of the extension relative to the coupling device. In another variation, the grooves may be sized in a manner that permits retention thereby of the extension; however that extension may pivot about the button within the grooves. Such a variation permits varus/valgus movement of the strut, and further allows the wearer to lean to either direction when wearing the support during the course of use.

Figure 15:
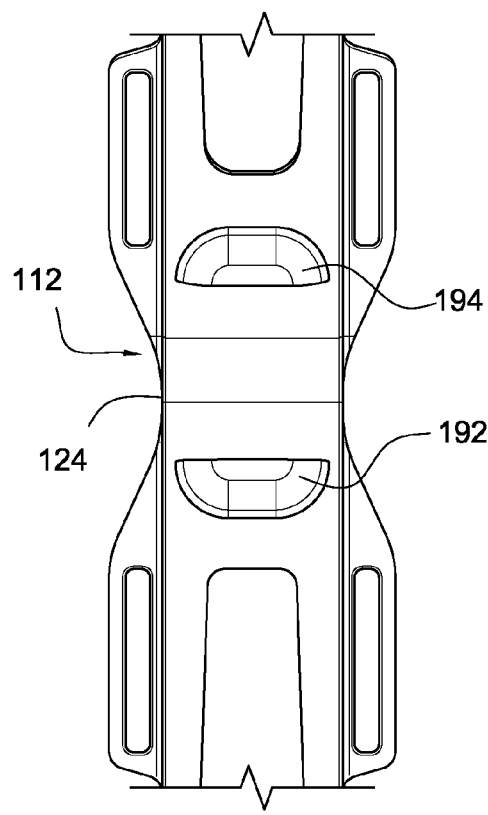
FIG. 15 is a partial elevational view showing another variation of the posterior strut.

In accordance with another variation of the posterior strut 112, FIG. 15 illustrates the posterior strut 112 as defining first and second receiving portions 192, 194 which are opposed from one another and located on the first and second strut segments, respectively. The receiving portions 192, 194 are arranged to closely retain a resilient device adjacent to the first surface of the posterior strut in a low profile. The low profile is achieved at least in part by the widened form of the receiving portions which only extend a short distance from the first surface of the posterior strut. The low profile allows for minimal extension of any components from the leg support thereby reducing any possible interference to the wearer when involved in physical activities.

Figure 16:
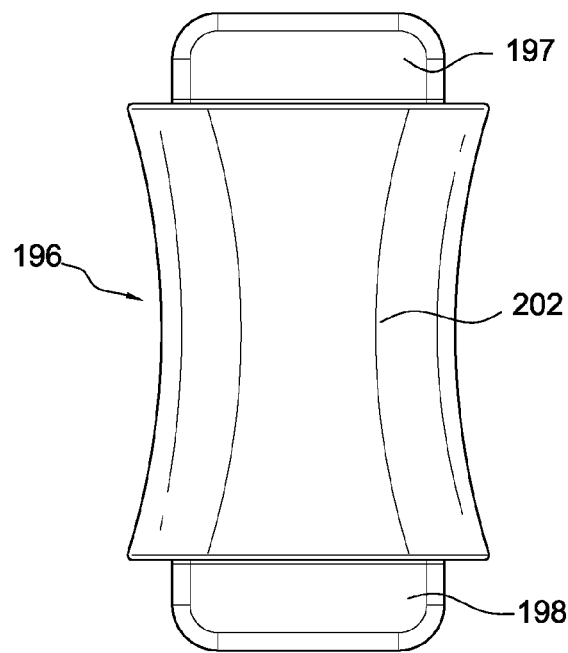
FIG. 16 is an elevational view showing an embodiment of a resilient insert.
Figure 17:
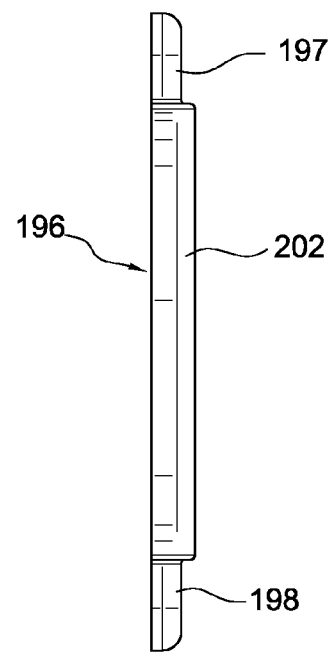
FIG. 17 is a side elevational view showing the resilient insert of FIG. 16.

Turning to FIGS. 16 and 17, a resilient insert 196 is shown having cut-away extensions 197, 198 at the end portions thereof which are configured to snugly secure individually with and place the resilient insert 196 between the receiving portions 192, 194 illustrated in FIG. 15. The resilient insert 196 has contours 202 which facilitate bending of the resilient insert at the center portion thereof.

As particularly exemplified in FIG. 17, the resilient insert likewise has a low profile which and a minimal thickness. The low profile of the resilient insert is consistent with the receiving portions which have a widened form and only provide a short distance from the first surface of the posterior strut. The low profile nature of this embodiment allows for minimal extension of any components from the leg support thereby reducing any possible interference to the wearer when involved in physical activities.

Figure 18:
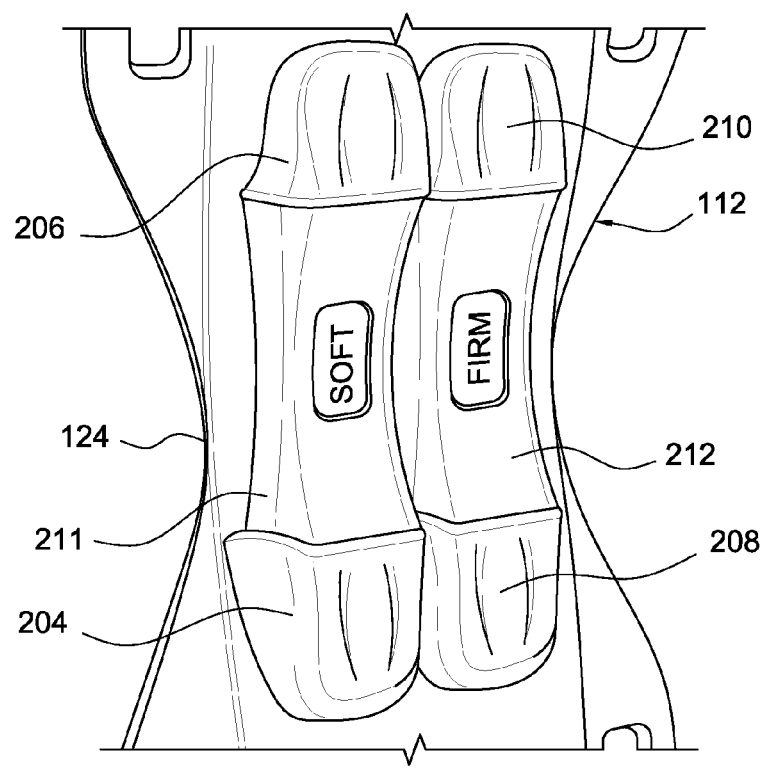
FIG. 18 is a partial elevational view showing another variation of the posterior strut and resilient inserts.

In accordance with another embodiment, FIG. 18 illustrates the posterior strut 124 as having a pair of opposed receiving portions 204, 206, 208, 210. Each pair of receiving portions is arranged to receive an elongate resilient insert 211, 212. The resilient inserts 211, 212 may have different stiffnesses relative to one another so as to accommodate or provide different stiffnesses for the lateral and medial aspects of the leg. As mentioned above in connection with the embodiments of FIGS. 5D and 5E, depending on the physical activities, the lateral and medial aspects of the knee may require different support which is obtained by different resilient inserts.

Figure 19:
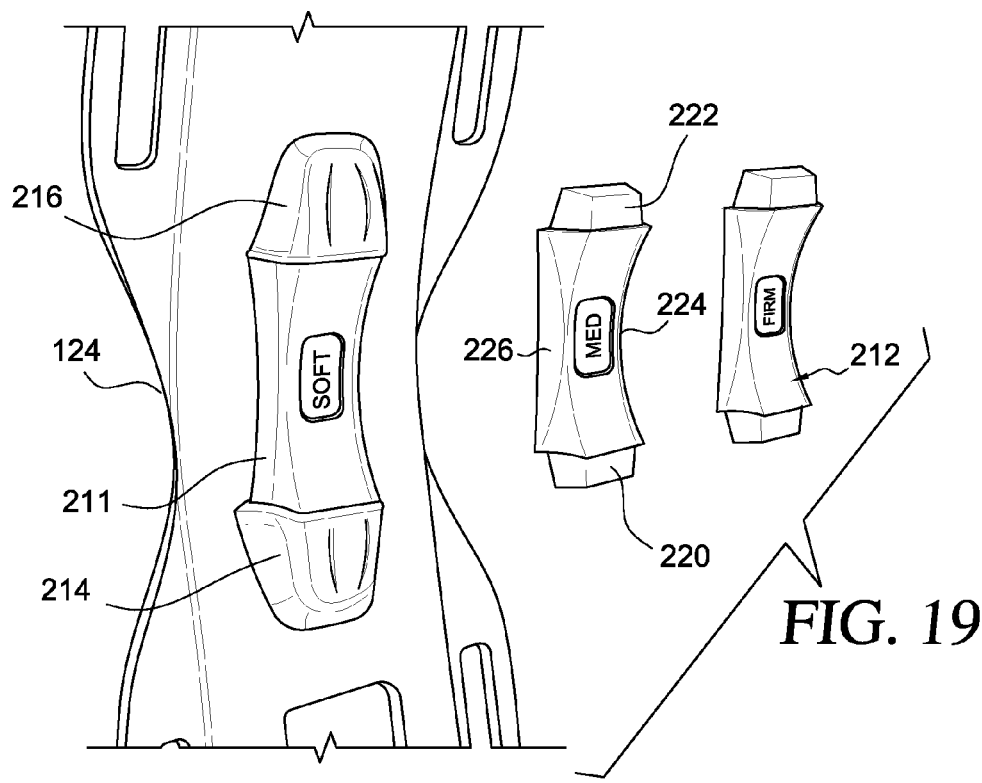
FIG. 19 is a partial elevational view showing another variation of the posterior strut and resilient inserts.

FIG. 19 illustrates yet another embodiment wherein the posterior strut 124 has only first and second receiving portions 214, 216 which are opposed from one another on the first surface of the strut and located along a central longitudinal axis of the posterior strut. A resilient insert 211, 212, 224 is adapted to be snugly secured within the receiving portions via cut-away extensions 220, 222. Each of the resilient inserts 211, 212, 224 have a generally arcuate contour which facilitates bending. Moreover, each of the resilient inserts 211, 212, 224 are appropriately labeled with indicia 226 according to their stiffness.

It is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. The skilled artisan will recognize the interchangeability of various features from different embodiments.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A leg support adapted to be secured to a leg, comprising:
    an elongate and continuous strut having first and second rigid or semi-rigid segments, and a flexible middle segment located therebetween, the strut arranged for securing to a posterior side of a leg and centrally located along a medial-lateral plane of a leg; and
    a resilient device secured to the strut against a first surface thereof, the resilient device extending across a length of the middle strut segment, the resilient device having a predefined shape;

wherein upon bending due to a load, the resilient device urges the strut into a generally upright configuration corresponding to extension of a leg, the resilient device returning to the predefined shape after the load is released therefrom.

2. The leg support according to claim 1, further comprising a coupling device arranged to be secured to footwear and connecting to a first end portion of the first strut segment.

3. The leg support according to claim 2, wherein the first strut segment is releasable from the coupling device.

4. The leg support according to claim 2, further comprising:
an attachment device secured to and slidable along the first end portion of the first strut segment; and
an elongate extension adjustably secured to the attachment device and connecting to the coupling device.

5. The leg support according to claim 4, wherein the extension is pivotable relative to the coupling device.

6. The leg support according to claim 1, wherein the middle strut segment has a thinned thickness relative to the first and second segments.

7. The leg support according to claim 6, wherein the resilient device is selectively activated against the middle strut segment, the resilient device being movable relative to the middle strut segment between an activated placement and a deactivated placement.

8. The leg support according to claim 1, wherein the resilient device is selectively aligned with the strut, the resilient device having a first end pivotally attached to the second strut segment.

9. The leg support according to claim 1, wherein the resilient device has a protruding portion located at a first end portion engaging a first receiving portion located on the first strut segment, a second end portion of the resilient device connecting to a second receiving portion located on the second strut segment.

10. The leg support according to claim 9, wherein the first receiving portion defines an arcuate slot formed by the first strut segment and arranged to receive the protruding portion.

11. The leg support according to claim 9, wherein the second end portion of the resilient device has a rotatable locking element permitting the resilient device to pivotally and removably connect to the second strut segment.

12. The leg support according to claim 9, wherein the first receiving portion defines a bracket protruding outwardly from the first strut surface and arranged to receive the protruding portion of the resilient device.

13. The leg support according to claim 1, wherein the resilient device is a polymeric spring element having a predefined configuration, the resilient device arranged for bending and resiliently returning to the predefined configuration.

14. The leg support according to claim 1, wherein the resilient device has different stiffnesses located on first and second sides corresponding to lateral and medial aspects of a leg.

15. The leg support according to claim 14, wherein the first resilient device side has a greater stiffness than the second resilient device side.

16. A leg support adapted to be secured to a leg, comprising:
an elongate strut having first and second rigid or semi-rigid segments, and a flexible middle segment located therebetween, the strut being arranged for securing to a posterior side of a leg generally and centrally located along a medial-lateral plane of a leg, and a second surface of the strut arranged adjacent the leg of the wearer; and
a monolithic polymeric resilient insert device removably secured against a first surface of the strut and extending across the middle strut segment, the resilient device having a predefined shape;
wherein upon bending due to a load, the resilient device urges the strut into a generally upright configuration corresponding to extension of a leg, the resilient device returning to the predefined shape after the load is released therefrom;
wherein the resilient device has a protruding portion located at a first end portion engaging a first receiving portion located on the first strut segment, a second end portion of the resilient device connecting to a second receiving portion located on the second strut segment.

17. The leg support according to claim 16, further comprising a posterior thigh shell adjustably secured along at least a portion of the first strut segment.

18. The leg support according to claim 16, further comprising an anterior thigh shell connecting to the strut via a strapping system located between the posterior thigh shell and the resilient device.

19. A leg support adapted to be secured to a leg and footwear, comprising:
an elongate strut having first and second segments, and a flexible middle segment located therebetween, the strut being arranged for securing to a posterior side of a leg generally and centrally located along a medial-lateral plane of a leg;
a resilient polymeric spring element removably secured to the strut, the spring element corresponding to the middle strut segment generally along a first strut surface, the spring element having a predefined configuration, the spring element arranged for bending and resiliently returning to the posterior strut into a predefined configuration;
an attachment device secured to and slidable along the first end portion of the first strut segment;
a coupling device arranged to be secured to footwear and connecting to a first end portion of the first strut segment; and
an elongate extension adjustably secured to the attachment device and pivotally connecting to the coupling device.

20. The leg support according to claim 19, wherein spring element is generally flat and has portions approximating the width of the strut.

* * * * *